United States Patent [19]

Heuvelsland et al.

[11] 4,393,249

[45] Jul. 12, 1983

[54] PROCESS FOR REMOVING ALKYNES FROM C₄ HYDROCARBON MIXTURES

[75] Inventors: Albert Heuvelsland, Heikant; Fritz F. F. Jann, Terneuzen, both of Netherlands; Greet de Block-Martens, Stekene, Belgium

[73] Assignee: The Dow Chemical Company, Midland, Mich.

[21] Appl. No.: 314,288

[22] Filed: Oct. 23, 1981

[51] Int. Cl.³ .......................... C07C 41/08; C07C 7/00
[52] U.S. Cl. .................................. 568/688; 568/403; 568/404; 568/467; 568/671; 568/672; 568/673; 568/657; 568/579; 585/843; 585/855; 585/864; 585/866; 423/245; 423/462; 560/242

[58] Field of Search ............... 568/688, 672, 673, 671, 568/467, 322, 361, 362, 403, 404, 405, 657, 579; 585/855, 843, 864, 866; 423/245 S, 262; 560/242

[56] References Cited

U.S. PATENT DOCUMENTS

| | | | |
|---|---|---|---|
| 2,098,842 | 11/1937 | Walter | 568/467 |
| 2,191,053 | 2/1940 | Walter | 568/688 |
| 4,112,009 | 9/1978 | Rescalli et al. | 585/855 |

*Primary Examiner*—Howard T. Mars
*Attorney, Agent, or Firm*—Charles J. Enright

[57] ABSTRACT

A process for removing alkynes from hydrocarbon mixtures, particularly those containing butadiene by reacting the alkynes with hydroxyl group containing organic compounds in the presence of a silver exchanged ion-exchange resin and separating the products formed from the unreacted components of said mixture.

21 Claims, No Drawings

PROCESS FOR REMOVING ALKYNES FROM C4 HYDROCARBON MIXTURES

BACKGROUND OF THE INVENTION

This invention relates to an improved process for reacting alkynes with a hydroxyl compound in the presence of a catalyst and to an improved process for separating alkynes from fluid mixtures.

Hydrocarbon conversion processes yield crude $C_4$ fractions which contain valuable components such as butadiene. A typical such fraction is that given in Table I.

TABLE I

| Component | Volume Percentage | Boiling Point °C. |
|---|---|---|
| 1,3-butadiene | 39.1 | −4.4 |
| isobutylene | 27.7 | −6.9 |
| 1-butene | 17.2 | −6.3 |
| trans-2-butene | 6.0 | +0.9 |
| cis-2-butene | 4.5 | +0.9 |
| n-butane | 4.1 | −0.5 |
| $C_3$ hydrocarbons | 0.9 | — |
| $C_4$ acetylene | 0.2 | +5.1 |
| $C_5$ hydrocarbons | 0.1 | — |
| 1,2-butadiene | <0.1 | +10.9 |

1,3-Butadiene is a commercial valuable chemical which ranked 31st in order of high volume chemicals produced in the United States in 1975. 1,3-Butadiene is of great importance in synthetic rubber manufacture generally requiring a minimum purity of at least 99.0 weight percent. Generally, the maximum allowable amount of acetylenes as trace impurities is 500 ppm. Higher amounts cause undesirable polymerization of the acetylene contributing to equipment fouling and foaming problems.

A common method of purifying 1,3-butadiene from a $C_4$ hydrocarbon stream is a two-stage extractive distillation process. In this process, butanes, butenes and generally compounds less polar than butadiene are removed by extractive distillation with an appropriate solvent. Next, a second extractive distillation is utilized to remove alkynes and those compounds more polar than 1,3-butadiene. This two-step process is rather energy intensive which results in additional capital costs for heat recovery in order to minimize operational costs. Also alkynes such as vinylacetylene and diacetylene are unstable compounds which can be highly dangerous when concentrated. In order to lessen the above-mentioned problem, some loss of butadiene must be tolerated in order to remove the alkynes at low concentrations. Conventional purification processes are outlined in greater detail in The Kirk-Othmer Encyclopedia of Chemical Technology, Vol. 4, 3rd Ed., p. 326 (1978).

In 1966 a process was proposed in U.S. Pat. No. 3,273,314 (Quinn) involving the removal of alkynes by absorption with a silver carboxylate ion-exchange resin. This process is primarily directed toward the removal of alkynes from gaseous streams such as ethylene or helium. The process has the disadvantages of requiring frequent regeneration due to exhaustion of the alkyne capacity of the resin. Regeneration requires treatment with nitric acid and necessitates removal of the resin being regenerated from operation. This regeneration is both time consuming and costly.

In 1969, U.S. Pat. No. 3,458,591 (Bebb et al.) proposed a method for removing alpha-acetylenes from a hydrocarbon mixture containing 1,2-butadiene by a separation process which utilized an aqueous solution of sulfuric acid containing mercuric ions. Following contact with this solution, a phase separation allows the treated hydrocarbon to be separated from the acid layer. Bebb et al. proposed the following reaction:

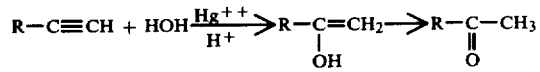

Apparently the above reaction forms products which are more polar and therefore segregate in a phase separate from that of the desired product. The Bebb method requires contact times of at least an hour and preferably at least two hours with very efficient agitation to effectively remove alkynes. If less efficient agitation is employed, much longer contact times are required. Other disadvantages are the extra environmental and safety precautions required by the use of mercury compounds which are extremely toxic.

During 1977 and 1978 four U.S. patents assigned to Snam Progetti, S.p.a., issued relating to the removal of alkynes from hydrocarbon mixtures having U.S. Pat. Nos. 4,020,114 (Rescalli I); 4,031,157 (Rescalli II); 4,066,713 (Rescalli III) and 4,112,009 (Rescalli IV).

Rescalli I proposed a process for the separation of butadiene from a $C_4$ hydrocarbon stream involving a sequential etherification of isobutylene and the acetylenic compounds followed by a distillation step. Rescalli II is directed to a method for removing acetylenic compounds from hydrocarbon mixtures involving etherification with an alcohol or glycol with removal of the formed ethers by distillation. Rescalli III involves removal of acetylenic compounds contained in inorganic or organic hydrocarbon streams characterized in that an organic acid is added to the acetylenic compounds. Rescalli IV is directed to a method for removing acetylenic compounds from hydrocarbons by reacting the acetylenic compounds with compounds of the formula R—OH wherein R is acetyl and thereafter removing the products. Common to all Rescalli patents I, II, III and IV is the feature of contacting the reactants of each process with an acid ion-exchange resin containing mercuric ions. All four patents prefer that such ion-exchange resin have polystyrene or polyphenolic matrix and three prefer also a divinylbenzene matrix. All four also prefer that the matrix have as substituents sulfonic groups (—$SO_3H$) and mention that resins having pendant —COOH groups are also useful.

All of these processes have the disadvantage of working with mercury whose toxicity is well-known. Also ion-exchange resins containing mercuric ions are not as selective toward alkyne conversion as is desired with isobutylene also being converted.

SUMMARY OF THE INVENTION

According to the present invention, a process comprising contacting an alkyne with hydroxyl compounds such as water or an organic compound containing at least one hydroxyl group under reaction conditions to form an ether, aldehyde, ketone or other oxygen-containing compound is improved by making such contact in the presence of a polymeric material having pendant anionic moieties with associated silver ions. This polymeric material having associated silver ions is environmentally safer than mercury compositions. Also this material is very active toward catalyzing the reaction of hydroxyl compounds with alkynes as well as being relatively selective for alkynes. With $C_4$ hydrocarbon streams it has a further advantage of longevity, maintaining its catalytic activity for long periods of time without necessitating regeneration.

DETAILED DESCRIPTION OF THE INVENTION

The invention employs as a reactant hydroxyl compounds, i.e., water or an organic compound containing at least one hydroxyl group which may be represented as R—OH, where R represents hydrogen or an organic group and may be alkyl, acyl, aryl, cycloalkyl or combinations thereof and may have various substituents. Any compound which contains a hydroxyl group reactive with an alkyne may be used, but it is preferable to use one which contains no other groups that are more reactive than the hydroxyl group with respect to the alkyne. Preferred are water, the alcohols, glycols and carboxylic acids with methanol being most preferred.

The invention also employs as a reactant an alkyne or mixtures thereof either alone or in combination with other organic or inorganic compounds. Suitable compounds or mixtures of compounds having alkynes mixed therewith include ethylene, helium and hydrocarbon streams. The preferred mixture is a $C_4$ fraction such as that produced by hydrocarbon conversion processes containing alkynes. A typical example of a $C_4$ stream is given in Table I, supra. The preferred alkyne reactants are propyne, 1-butyne and vinylacetylene.

The invention employs as a catalyst a polymeric material having pendant anionic moieties with associated silver ions. Examples of such polymeric materials include polyethylenes, polyphenols and polystyrenes. Copolymers may also be used such as styrene-divinylbenzene copolymers. These polymeric materials may also have pendant attached groups such as carboxylic (—COOH) or sulfonic (—$SO_3H$) groups. These polymeric materials also known as ion-exchange resins are manufactured by many techniques and sold under a variety of tradenames. One example of such a copolymer resin is DOWEX ® MSC-1 (trademark of The Dow Chemical Company) brand copolymer resin which is manufactured by The Dow Chemical Company of Midland, Mich. DOWEX MSC-1 cation-exchange resin is a sulfonated, macroporous, highly cross-linked styrene-divinylbenzene copolymer. Another suitable polymeric material is that manufactured by the Rohm and Haas Company of Philadelphia, Pa. under the tradename Amberlyst 15. Reference is made to U.S. Pat. No. 3,549,562 as teaching a typical process for manufacture of suitable polymeric materials and that teaching is hereby incorporated. U.S. Pat. No. 3,409,691 contains a further description of said resins including a silver ion associated resin and some of the known utilities. Typically ion-exchange resins are available in hydrogen form, but may be converted from hydrogen or other ionic forms, e.g., sodium, to the silver form used in the process of the invention by conventional ion-exchange techniques already known to those skilled in the art. The amount of resin converted can be varied. The optimum degree of exchange for a process of the invention as well as optimization of other process parameters is within the skill of the art and deemed an obvious modification of the invention. The preferred catalyst used in the process of the invention is a macroporous, highly cross-linked styrene-divinylbenzene copolymer resin having pendant sulfonate groups with associated silver ions such as silver exchanged DOWEX ® MSC-1. It is preferred that a predominant amount of the ion-exchangeable cations associated with said resin be silver ions. In an embodiment of the invention in which alkynes are being removed from $C_4$ hydrocarbon streams, it is especially preferred that substantially all cations available for ion-exchange be silver ions. Resins which are less than 100 percent exchanged with silver ions are suitable but tend to promote methyl-tertiary butyl ether (MTBE) formation.

It is to be noted that the reaction may be advantageously carried out in batch, semi-batch or continuous reactors.

The reaction may be carried out over a wide range of temperature. The operational temperature will depend upon the particular reactants used and the composition of the mixtures containing these reactants as well as other process parameters. For example, in one embodiment of the invention in which removal of various alkynes is desired from a hydrocarbon mixture containing butadiene, polymerization of butadiene occurs at temperatures of 90° C. and higher especially with long residence times. In general, an embodiment of the invention used to remove alkynes from $C_4$ stream will find suitable temperatures over a range of from about 30° C. to about 90° C. and a preferred temperature range of from 60° C. to about 80° C. At temperatures below 30° C., reaction rates become slow; while at temperatures above 90° C. in addition to dimerization of alcohol reactants, the equilibrium shifts to favor the reverse reaction.

The reaction may also proceed under elevated or depressed as well as atmospheric pressures. It is preferred, however, to run the process at a pressure sufficient to maintain the reaction mixture in a liquid phase. In gas phase with a $C_4$ hydrocarbon stream, polymerization may cause deactivation of the catalyst.

Reaction parameters such as temperature and pressure will generally be based upon practical considerations such as convenience, economy, particular reactants used and other process variables chosen. In any case, the optimum values chosen for each set of conditions and reactants is easily determined by one skilled in the art.

Also the molar or weight ratios of the reactants may vary. However, it is desirable to work in an excess of the hydroxyl compound. Also, where the alkynes are contained in a mixture of other compounds, it is preferred to have enough hydroxyl compound to ensure complete resin saturation. For a typical $C_4$ stream containing alkynes such as that given in Table I, the preferred hydroxyl-containing reactant to hydrocarbon feed content is about 4 moles per liter or higher.

Suitable contact of the reaction mixture with the aforementioned polymeric material ranges from a weight hourly space velocity (WHSV) from about 0.5 per hour to about 5.0 per hour. The WHSV =

$$\frac{[(\text{mass of total fluid stream} + \text{hydroxyl compound})/\text{hr}]}{(\text{catalyst mass})}$$

The actual WHSV utilized will of course depend upon other parameters such as the reactants chosen, the amount of dilution of the reactants in other media, temperature, etc. Tables II and Table III present conversion data for acetylenes removal on a silver exchanged resin at two different temperatures.

TABLE II

| | (60° C.) | | | |
| | Component Conversion (%) | | | |
| WHSV (h$^{-1}$) | propyne | 1-butyne | vinyl-acetylene | iso-butylene |
|---|---|---|---|---|
| 3.40 | 100 | 56 | 11 | 5 |
| 1.92 | 100 | 75 | 22 | 9 |
| 0.90 | 100 | 90 | 39 | 16 |
| 0.45 | 100 | 93 | 70 | 28 |

TABLE III

| | (80° C.) | | | |
| | Component Conversion (%) | | | |
| WHSV (h$^{-1}$) | propyne | 1-butyne | vinyl-acetylene | iso-butylene |
|---|---|---|---|---|
| 3.28 | 100 | 84 | 41 | 19 |
| 1.84 | 100 | 92 | 58 | 29 |
| 0.80 | 100 | 94 | 90 | 57 |
| 0.25 | 100 | 95 | 99 | 85 |

From the Tables, propyne is shown to be a very reactive alkyne with substantially all propyne from a C$_4$ hydrocarbon stream being converted even at high weight hourly space velocities and low temperatures. It is also seen that a higher WHSV less isobutylene is converted.

In a study of etherification of butadiene with a methanol/pentane/butadiene mixture, no less of commercially valuable butadiene was detected at 80° C. with about a 3 percent loss of butadiene due to polymerization at 90° C. and long residence times.

The oxygen-containing reaction products such as ethers, ketones, etc., formed in the process of the invention may be removed from the process effluent by conventional techniques such as distillation.

Therefore, the most preferred conditions for utilizing the process of the invention for removal of alkynes from C$_4$ hydrocarbon streams are as follows:

(1) reacting 4 moles or more of a C$_1$-C$_4$ monohydric aliphatic alcohol per liter of a C$_4$ hydrocarbon stream containing alkynes such as that given in Table I, (2) in the presence of a substantially completely silver exchanged, macroporous, highly cross-linked, sulfonated, styrene-divinylbenzene ion-exchange resin, (3) at a temperature from about 60° C. to about 80° C., (4) under sufficient pressure to maintain the reaction mixture in a liquid phase, and (5) at a WHSV of from about 0.5 to about 5.0 with subsequent removal of the formed ethers by conventional means.

The following examples are given to illustrate the advantages of the invention, but should not be construed as limiting the scope.

In each of the following examples the resins are fully exchanged by conventional means to the particular form of interest.

EXAMPLE 1

Several forms of DOWEX ® MSC-1 resin were utilized to catalyze the reaction of methanol with alkynes in a C$_4$ hydrocarbon stream. Process parameters were varied. The feed stream ranged from 90 to 50 percent C$_4$ stream with the balance being methanol. Temperatures were varied from 50° C. to 90° C. and the weight hourly space velocity (WHSV) was varied from 0.5 to 5.0 hr$^{-1}$. The pressure was kept sufficient to maintain a liquid phase. Results are shown in Table IV.

TABLE IV

| Cation | Electron Configuration | Activity toward removal of | |
|---|---|---|---|
| | | Acetylenes | Isobutylenes |
| H$^+$ | — | none | good |
| Ni$^{++}$ | [Ar]3d$^8$ | slightly above 80° C. | |
| Cu$^+$ | [Ar]3d$^{10}$ | only initial activity | |
| Cu$^{++}$ | [Ar]3d$^9$ | none | above 80° |
| Ag$^+$ | [Kr]4d$^{10}$ | good | good |
| Zn$^{++}$ | [Ar]3d$^{10}$ | none | none |
| Cd$^{++}$ | [Kr]4d$^{10}$ | none | none |
| Hg$^{++}$ | [Xe]4f$^{14}$5d$^{10}$ | good | good |
| Tl$^{+++}$ | [Xe]4f$^{14}$5d$^{10}$ | none | slight |

From Table IV it is seen that only Ag$^+$ and Hg$^{++}$ gave good activities toward acetylene conversion. These two catalysts, however, behave differently with respect to the conversion of isobutylene versus acetylene. The Ag$^+$ resin favors the acetylene reaction over the alkene reaction with the opposite true for the Hg$^{++}$ resin.

EXAMPLE 2

A C$_4$ hydrocarbon feedstock containing 630 ppm propyne, 1430 ppm 1-butyne and 6600 ppm vinylacetylene was fed with methanol in a 80:20 weight percent ratio to a reactor containing silver exchanged DOWEX ® MSC-1 resin at 80° C. and at a weight hourly space velocity of 0.25 hour$^{-1}$. Analysis of the effluent composition showed 0 ppm propyne, 82 ppm 1-butyne and 8 ppm vinylacetylene, while none of the original butadiene had reacted.

EXAMPLE 3

A butadiene feedstock containing 10 percent pentane is added to methanol in an 85:15 weight percent ratio and is fed under pressure (p=15 bar) to a reactor containing the Ag$^+$ form of DOWEX ® MSC-1 at 70° C. and at a WHSV=1.4 hr$^{-1}$. The effluent analyzed by conventional means shows that essentially none of the original butadiene reacts.

EXAMPLE 4

A C$_4$ hydrocarbon feedstock containing 820 ppm propyne, 1370 ppm 1-butyne, 6140 ppm vinylacetylene and 23.5 percent isobutylene is fed together with 25 percent methanol to a reactor containing the Ag$^+$ form of DOWEX ® MSC-1 at 80° C. and at a WHSV=0.9 hr$^{-1}$. The effluent analysis shows 100 percent conversion for propyne, 90.5 percent for 1-butyne, 99.3 percent for vinylacetylene and 29.5 percent for isobutylene while essentially none of the original butadiene reacts.

EXAMPLE 5

Comparative Example

A C$_4$ hydrocarbon feedstock containing 750 ppm propyne, 1330 ppm 1-butyne, 6050 ppm vinylacetylene and 22.9 percent isobutylene is added to methanol in a 75:25 weight percent ratio and then fed to a reactor containing the Hg$^{++}$ form of DOWEX ® MSC-1 at 70° C. and at a WHSV=4.0 hr$^{-1}$. The effluent analysis shows 100 percent for propyne, 80 percent for 1-butyne, 35 percent for vinylacetylene and 88 percent for isobutylene.

Further modifications of the invention disclosed will be apparent to those skilled in the art and all such modifications are deemed to be within the scope of the invention as defined by the following claims.

What is claimed is:

1. A process comprising contacting an alkyne with a $C_1$–$C_4$ monohydric alcohol or mixture thereof under reaction conditions to form an ether, said reactive process occurring in the presence of a catalytic amount of a cation-exchange resin having a plurality of pendant sulfonate groups with silver metal counterions.

2. A process as defined in claim 1 wherein said polymeric material is a styrene-divinylbenzene copolymer resin.

3. A process as defined in claim 2 wherein said alcohol is methanol.

4. A process for etherifying alkynes comprising contacting under conversion conditions an alkyne or mixture thereof with an organic compound containing at least one hydroxyl group in the presence of ion-exchange resin containing silver ions.

5. A process for the removal of alkynes from inorganic or organic mixtures or combination mixtures thereof comprising contacting under reaction conditions said alkyne-containing mixture with an organic compound having at least one hydroxyl group in the presence of a catalytic amount of a silver exchanged ion-exchange resin and thereafter removing the oxygen-containing products from said mixture.

6. A process for the removal of alkynes from fluid streams comprising contacting a fluid stream containing a plurality of alkynes with water, or an organic compound having at least one hydroxyl group or mixture thereof under conditions sufficient to convert said alkynes to oxygen-containing products and removing from the reaction mixture the products so formed, said reactive process occurring in the presence of a catalytic amount of a polymeric material having associated therewith silver ions.

7. A process as defined in claim 6 wherein said fluid stream is a hydrocarbon stream.

8. A process as defined in claim 7 wherein said hydroxyl compound is water or an organic compound having at least one hydroxyl group, said hydroxyl compound being of the formula R—OH wherein R is alkyl, acyl, aryl, cycloalkyl or combinations thereof or hydrogen.

9. A process as defined in claim 8 wherein said hydroxyl compound is a $C_1$–$C_4$ monohydric alcohol.

10. A process as defined in claim 9 wherein said hydrocarbon stream is a $C_4$ hydrocarbon stream.

11. A process as defined in claim 10 wherein said alcohol is methanol.

12. A process as defined in claim 10 wherein said oxygen-containing products are ethers.

13. A process as defined in claim 12 wherein said polymeric material is a cation-exchange resin having a plurality of pendant sulfonate groups with silver metal counterions.

14. A process as defined in claim 13 wherein said polymeric material is a styrene-divinylbenzene copolymer resin.

15. The process of claim 1 wherein the reaction conditions include a temperature less than about 90° C.

16. The process of claim 5 wherein the reaction conditions include a temperature less than about 90° C.

17. The process of claim 16 wherein the reaction conditions include a temperature of from about 30° C. to about 90° C.

18. The process of claim 17 wherein the reaction conditions include a temperature of from about 60° C. to about 80° C.

19. The process of claim 6 wherein the conditions include a temperature of less than about 90° C.

20. The process of claim 19 wherein the conditions include a temperature from about 30° C. to about 90° C.

21. The process of claim 20 wherein the conditions include a temperature from about 60° C. to about 80° C.

* * * * *